United States Patent
Cojocaru et al.

(10) Patent No.: US 10,158,093 B2
(45) Date of Patent: Dec. 18, 2018

(54) METHOD FOR MANUFACTURING AN ELECTRONIC DEVICE, PARTICULARLY A DEVICE MADE OF CARBON NANOTUBES

(71) Applicants: Ecole Polytechnique, Palaiseau (FR); Centre National de la Recherche Scientifique, Paris (FR); Institut Francais des Sciences et Technologies des Transports de l'Amenagement et des Reseaux, Champs-sur-Marne (FR)

(72) Inventors: Costel-Sorin Cojocaru, Palaiseau (FR); Fatima Zahra Bouanis, Châtillon (FR); Kitchner Max Garry Rose, Massy (FR)

(73) Assignees: Ecole Polytechnique, Palaiseau (FR); Centre National de la Recherche Scientifique, Paris (FR); Institut Francais des Sciences et Technologies des Transports de l'Amenagement et des Reseaux, Champs-sur Marne (FR)

( * ) Notice: Subject to any disclaimer, the term of this patent is extended or adjusted under 35 U.S.C. 154(b) by 0 days.

(21) Appl. No.: 15/516,921

(22) PCT Filed: Oct. 7, 2015

(86) PCT No.: PCT/IB2015/057665
§ 371 (c)(1),
(2) Date: Apr. 5, 2017

(87) PCT Pub. No.: WO2016/055951
PCT Pub. Date: Apr. 14, 2016

(65) Prior Publication Data
US 2017/0244056 A1    Aug. 24, 2017

(30) Foreign Application Priority Data
Oct. 8, 2014  (FR) ................................. 14 59658

(51) Int. Cl.
*B82Y 40/00* (2011.01)
*H01L 51/05* (2006.01)
(Continued)

(52) U.S. Cl.
CPC .......... *H01L 51/0558* (2013.01); *B82Y 10/00* (2013.01); *B82Y 40/00* (2013.01);
(Continued)

(58) Field of Classification Search
CPC ......... H01L 2221/68363; H01L 51/003; H01L 51/0048; G01N 27/4146; B82Y 40/00
See application file for complete search history.

(56) References Cited

U.S. PATENT DOCUMENTS

| 2006/0093545 | A1* | 5/2006 | Maruyama | ............. | B82Y 30/00 |
| | | | | | 423/447.3 |
| 2007/0048970 | A1 | 3/2007 | Suzuki et al. | | |

(Continued)

FOREIGN PATENT DOCUMENTS

| WO | 2012/173768 A2 | 12/2012 |
| WO | 2013/076164 A1 | 5/2013 |

OTHER PUBLICATIONS

SPI-Chem, "Single-Crystal Salt Crystals—NaCl Substrates-Rock Salt—SPI Supplies," https://web.archive.org/web/20060615074750/http://2spi.com/catalog/submat/substr.shtml, (3 pages)(2006).
(Continued)

*Primary Examiner* — Sonya D McCall Shepard
(74) *Attorney, Agent, or Firm* — Morgan, Lewis & Bockius LLP

(57) ABSTRACT

The invention relates to a method for manufacturing an electronic device, particularly a device including a flexible and/or low-cost substrate and/or carbon nanotubes, and also relates to electronic devices produced using said method.
(Continued)

Figure 1:
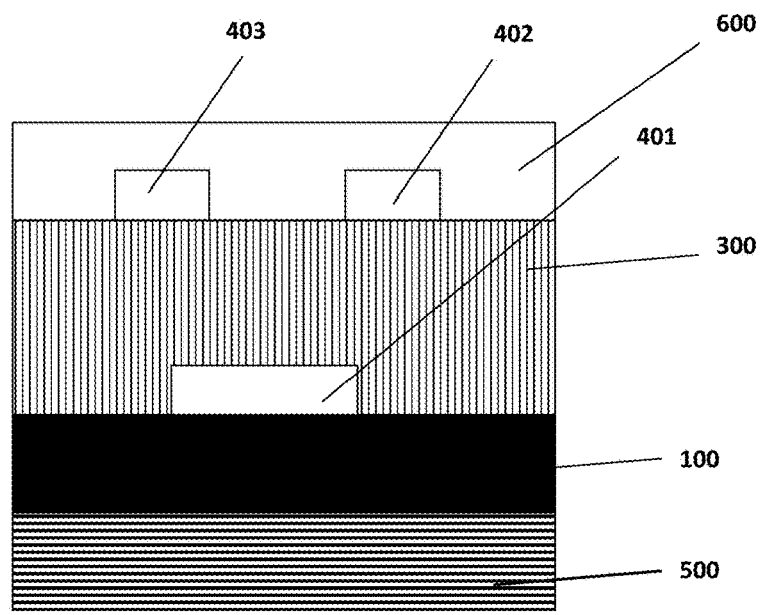

The method for manufacturing an electronic device, including a substrate mad of a material M and an active semiconductor material layer (3), includes the following steps: a) providing a carrier (10) made of an alkali metal salt or alkaline earth metal salt, preferably sodium chloride (NaCl) or potassium chloride (KCl); optionally, b) depositing a dielectric material layer (2) onto one surface of the carrier; c) forming an active semiconductor material layer (3) on one surface of the carrier when Step b) is not implemented or on the free surface of the layer when Step b) is implemented; d) forming different components of the electronic device on and/or under the layer; e) depositing a protective layer onto the layer stack, obtained in Step d), of the different components of the electronic device, said protective layer being made of the material M required for the substrate (1); and f) removing the carrier (10) by dissolving one or more of the components of said electronic device on a substrate different from the substrate (1). In said removal of the carrier, the method does not include any step for manufacturing one or more of the components of said electronic device on a substrate different from the substrate (1). The invention is of use in the field of electronics in particular.

14 Claims, 11 Drawing Sheets

(51) Int. Cl.
 *B82Y 10/00* (2011.01)
 *H01L 51/00* (2006.01)
 *H01L 29/16* (2006.01)
 *G01N 27/414* (2006.01)
 *H01L 51/10* (2006.01)
 *H01L 29/786* (2006.01)
 *H01L 27/12* (2006.01)
 *H01L 29/778* (2006.01)

(52) U.S. Cl.
 CPC ..... *G01N 27/4146* (2013.01); *H01L 27/1292* (2013.01); *H01L 29/1606* (2013.01); *H01L 29/78684* (2013.01); *H01L 51/003* (2013.01); *H01L 51/004* (2013.01); *H01L 51/0048* (2013.01); *H01L 51/0049* (2013.01); *H01L 51/0097* (2013.01); *H01L 51/0512* (2013.01); *H01L 51/0541* (2013.01); *H01L 51/0545* (2013.01); *H01L 51/102* (2013.01); *H01L 29/778* (2013.01)

(56) References Cited

U.S. PATENT DOCUMENTS

| 2007/0211189 | A1 | 9/2007 | Yamazaki et al. |
| 2010/0133511 | A1* | 6/2010 | Zhou ............ B82Y 10/00 257/24 |
| 2010/0255323 | A1 | 10/2010 | Nakamura et al. |
| 2012/0091436 | A1 | 4/2012 | Forrest et al. |
| 2012/0319096 | A1* | 12/2012 | Rinzler ............ B82Y 10/00 257/40 |

OTHER PUBLICATIONS

International Search Report issued in corresponding International Patent Application No. PCT/IB2015/057665 dated Jan. 5, 2016.

\* cited by examiner

METHOD FOR MANUFACTURING AN ELECTRONIC DEVICE, PARTICULARLY A DEVICE MADE OF CARBON NANOTUBES

The invention relates to a process for the manufacture of an electronic device, in particular comprising a flexible and/or inexpensive substrate and/or carbon nanotubes.

It also relates to the electronic devices obtained by this process.

Numerous electronic devices exist.

Mention may be made of transistors, in particular field effect transistors, sensors, inverters, and the like.

All these devices have it in common of comprising a substrate and an active layer made of a semiconductor material. In general, the substrate is an expensive rigid substrate, such as silicon wafers.

The miniaturization of these electrical devices, and also the appearance of a demand for such devices on flexible and/or inexpensive substrates, is currently expanding rapidly.

Thus, Fumiaki N. Ishikawa et al., "Transparent Electronics Based on Transfer Printed Aligned Carbon Nanotubes on Rigid and Flexible Substrates", ACS Nano, Vol. 3, No. 1, pp 73-78, describe a transparent thin film transistor in which the substrate is a transparent flexible substrate made of polyethylene terephthalate (PET).

They indicate that, due to the nature of the substrate, the process for the manufacture of the transistor has to be a low-temperature manufacturing process and that such a low-temperature manufacturing process would also make it possible to manufacture devices, in the case in point transistors, on paper and even on artificial skin.

In this paper, the active layer made of a semiconductor material consists of single-walled carbon nanotubes (SWNTC).

In the manufacturing process described, the SWNTC are first grown on a quartz substrate and then detached from this quartz substrate in order to be placed on a PET substrate on which had been formed beforehand a back door and a layer made of a dielectric material. The source and drain electrodes were then manufactured by photolithography.

This process exhibits at least three disadvantages.

The first disadvantage is that the manufacturing process described in this paper is difficult to carry out industrially as it is important, for an electronic device, for all the connections and the components to be perfectly positioned, which is only achievable when the support is a perfectly flat and rigid support. In point of fact, this is not the case for a flexible substrate as described in the paper by Fumiaki N. Ishikawa et al.

The patent application WO 2004/088728 then provided for the positioning of the flexible substrate on a rigid support and for the attaching of it thereto by an adhesive tape, then for the forming of the different components of the electronic device and, at the end of the procedure, for the removal of the rigid support.

However, this process exhibits the same disadvantages as that described in Fumiaki N. Ishikawa et al., namely that the temperatures of the manufacturing process have to be limited so as not to damage the flexible substrate. This is the second disadvantage.

The third disadvantage is that, by the technique for the transfer of the carbon nanotubes, the latter are no longer aligned, lose their length and thus their effectiveness as semiconductor material.

The invention is targeted at overcoming the disadvantages of the processes of the prior art by providing a process for the manufacture of electronic devices on a flexible and/or inexpensive substrate and/or a substrate which might be damaged, or even destroyed, by means of high temperatures and/or of aggressive conditions, in which process according to the invention methods for the formation of the different components can be used which require the use of high temperatures and/or of aggressive conditions, such as etching by acids, and the like.

In other words, all the processes for the manufacture of the different components of the electronic devices of the prior art, even those requiring the use of high temperatures and/or of conditions aggressive for the substrate, can be used in the process of the invention.

However, by virtue of the process of the invention, these high temperatures and/or these aggressive conditions will not damage or destroy the substrate.

Thus, by virtue of the process of the invention, high temperatures and/or aggressive conditions, which were limiting factors for the choice of the nature of the substrate in the processes of the prior art, can be used to manufacture the different components of the electronic devices.

To this end, the invention provides a process for the manufacture of an electronic device comprising:
a substrate made of a material M, and
an active layer made of a semiconductor material, characterized in that it comprises the following steps:
 a) provision of a support made of a salt of an alkali metal or alkaline earth metal,
 b) optionally deposition, on one face of the support, of a layer made of a dielectric material,
 c) formation, on one face of the support when step b) is not carried out or on the free face of the layer formed in step b) when step b) is carried out, of an active layer made of a semiconductor material,
 d) formation of the different components of the electronic device on and/or under the active layer made of a semiconductor material,
 e) deposition of a protective layer on the stack obtained in step d) of layers and of the different components of the electronic device, this protective layer being made of the material M desired for the substrate, and
 f) removal of the support,
and in that it does not comprise any step of formation of one of the components of the electronic device on a separate substrate.

In a first preferred alternative form of the process of the invention, the material M is made of a flexible material comprising an organic part, preferably chosen from polyimide, polyethylene terephthalate (PET), polyethylene naphthalate (PEN), polyvinyl chloride and poly(methyl methacrylate) (PMMA), preferably PMMA.

In a second preferred alternative form of the process of the invention, the substrate is an inexpensive material, preferably chosen from a metal, glass and paper.

Preferably, in all the alternative forms of the process of the invention, the support is made of an alkali metal or alkaline earth metal salt chosen from chloride, bromide, fluoride, iodide, oxide, hydroxide and carbonate salts, an alkali metal or alkaline earth metal chosen from magnesium, sodium and potassium.

Preferably, the support is made of NaCl or KCl.

Most preferably, the support is made of NaCl.

Also, in all the alternative forms of the process of the invention, the material of the dielectric layer is chosen from $Al_2O_3$ and $SiO_2$.

Still in all the alternative forms of the process of the invention, the active layer is made of a material chosen from graphene, carbon nanotubes, preferably single-walled carbon nanotubes, silicon, germanium, alloys of silicon and germanium, silicon carbide and organic semiconductor materials chosen from tetracene, anthracene, polythiophene, poly(3-hexylthiophene) (P3HT), poly[N-9'-heptadecanyl-2,7-carbazole-alt-5,5-(4',7'-di-2-thienyl-2',1',3'-benzothiadiazole)] (PCDTBT), poly[2-methoxy-5-(3',7'-dimethyloctyloxy)-1,4-phenylene-vinylene] (MDMO-PPV), poly[2-methoxy-5-(2-ethylhexyloxy)-1,4-phenylene-vinylene] (MEH-PPV), poly(3,4-ethylenedioxythiophene) (PEDOT), poly(3,4-ethylenedioxythiophene):poly(styrenesulfonate) (PEDOT:PSS), fullerenes, methyl [6,6]-phenyl-$C_{61}$-butyrate (PCBM), poly[oxa-1,4-phenylene-(1-cyano-1,2-vinylene)-(2-methoxy-5-(3,7-dimethyloctyloxy)-1,4-phenylene)-1,2-(2-cyanovinylene)-1,4-phenylene] (PCNEPV), polyfluorene and poly(styrenesulfonate) (PSS).

However, in a particularly preferred embodiment of the process of the invention, the active layer is made of single-walled carbon nanotubes.

In this case, the active layer of carbon nanotubes can be obtained by formation of a percolating network of carbon nanotubes formed from carbon nanotubes prepared separately.

However, preferably, the active layer of carbon nanotubes is obtained by growth of the carbon nanotubes directly on the surface of the support when step b) is not carried out or directly on the free surface of the layer made of a dielectric material when step b) is carried out.

Still preferably, the electronic device manufactured by the process of the invention is a transistor.

Preferably again, the electronic device manufactured by the process of the invention is a sensor comprising electrodes, to which the process of the invention additionally comprises, after step f), a step of functionalization of the electrodes with the desired substances.

Also preferably, the electronic device manufactured by the process of the invention is an inverter.

Figure 2:
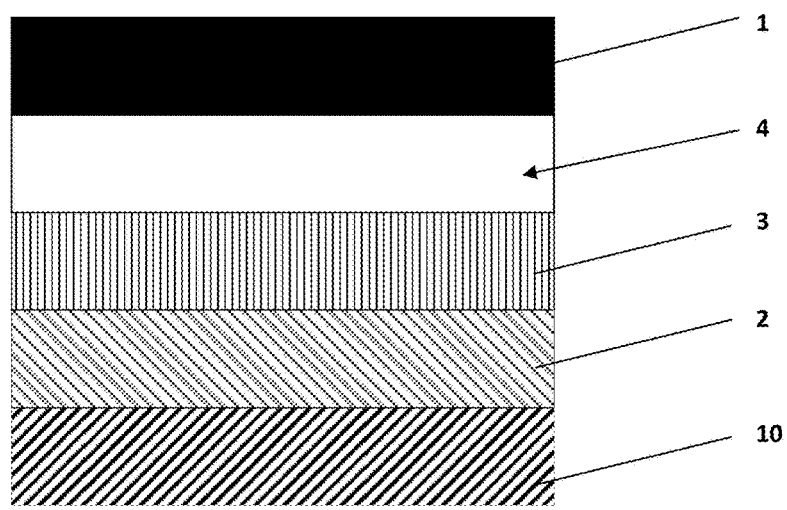
Figure 3:
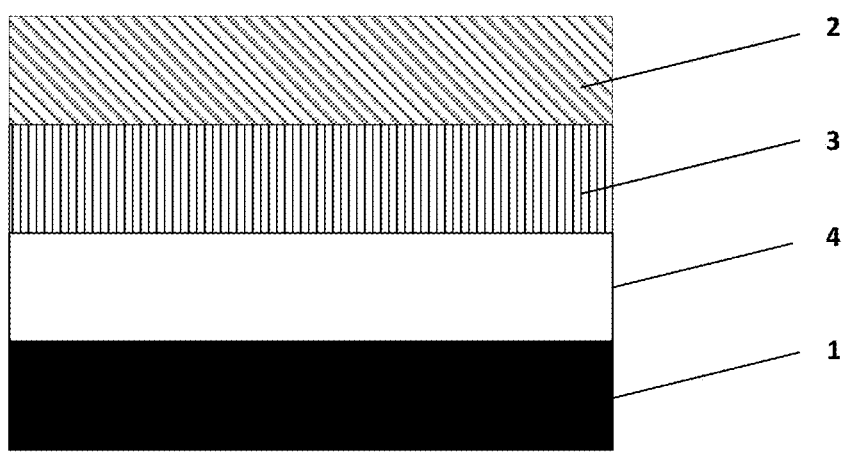
Figure 4:
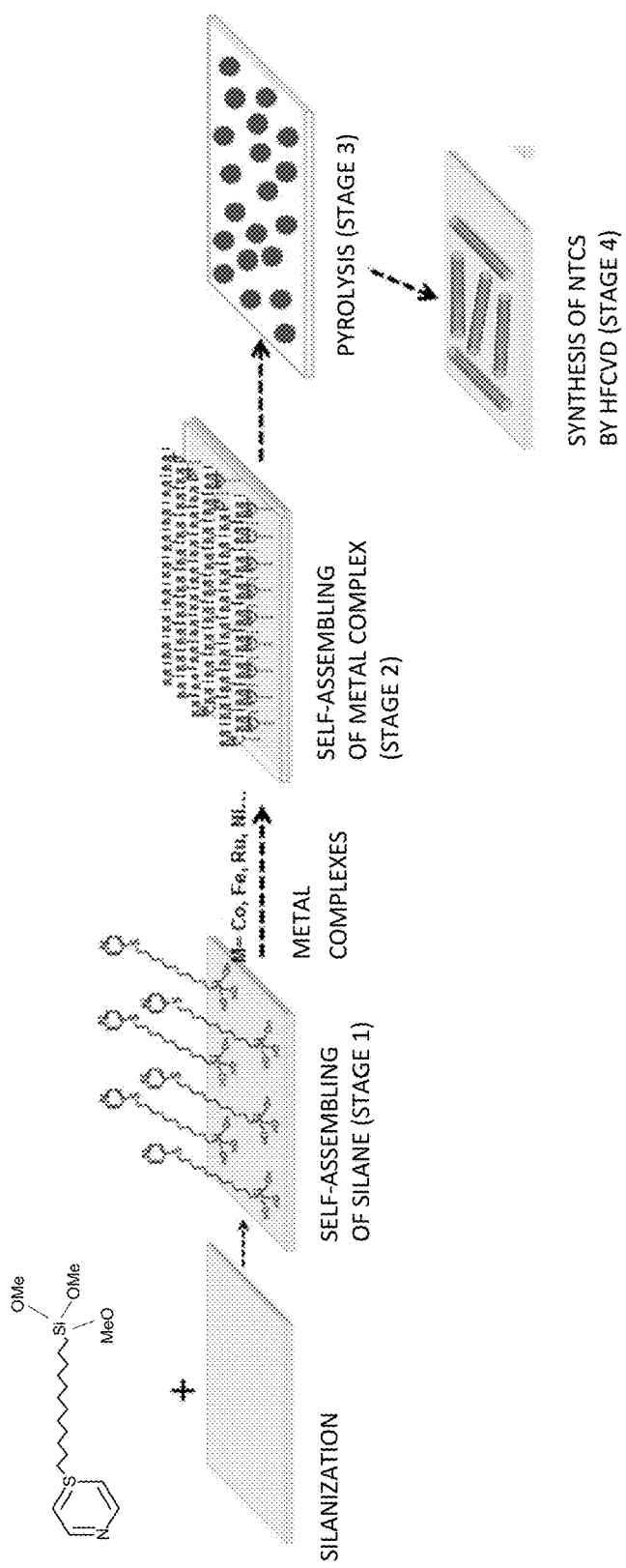
Figure 5:
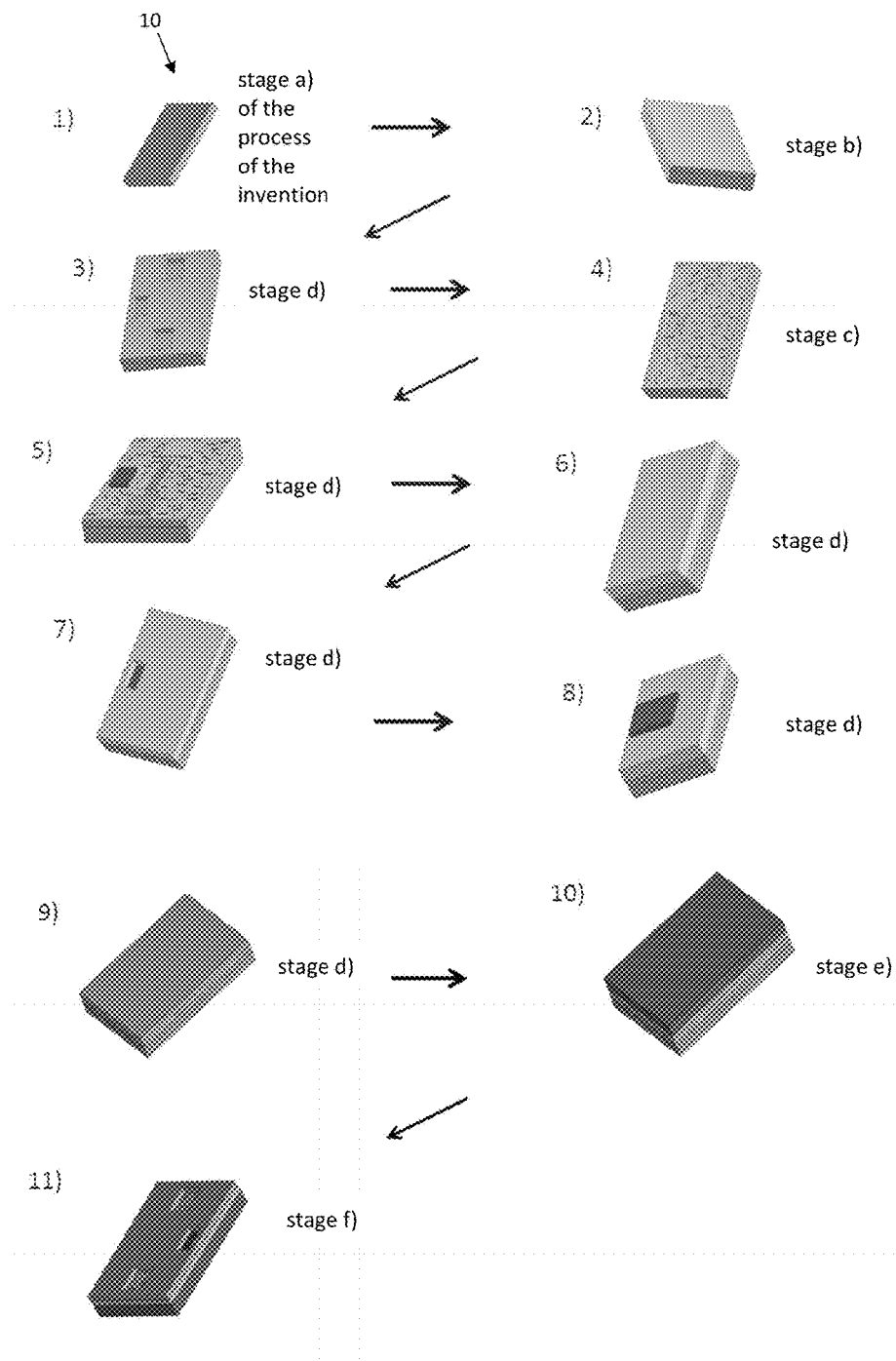
Figure 6:
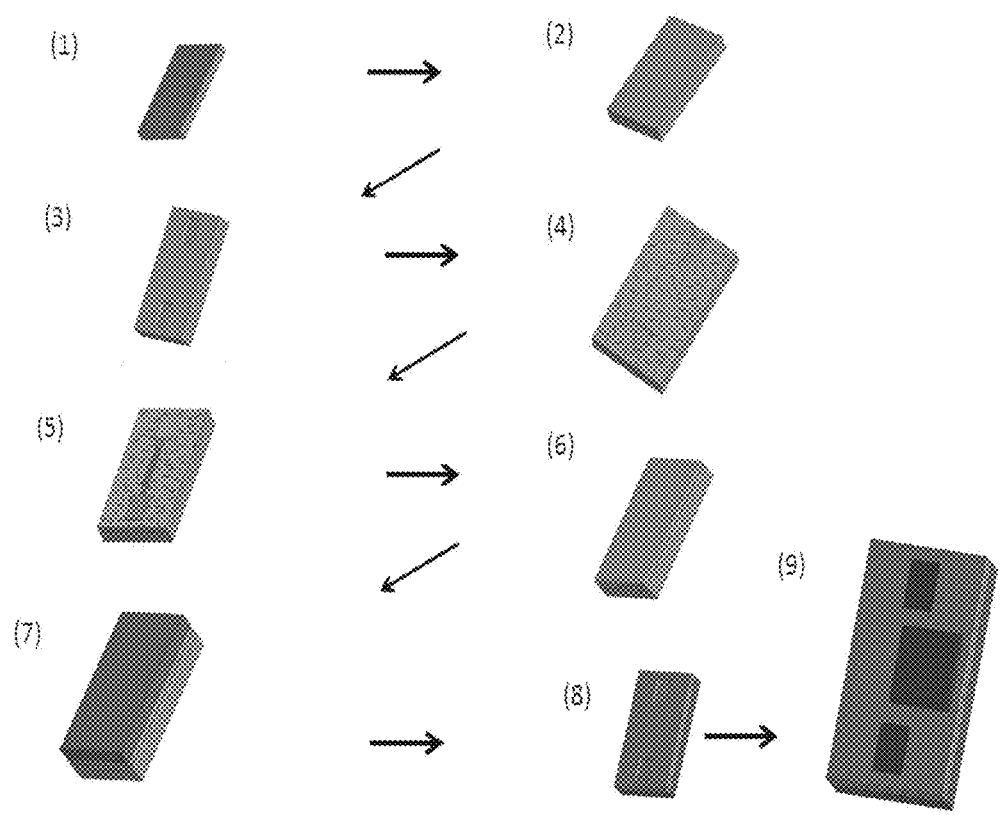
Figure 7:
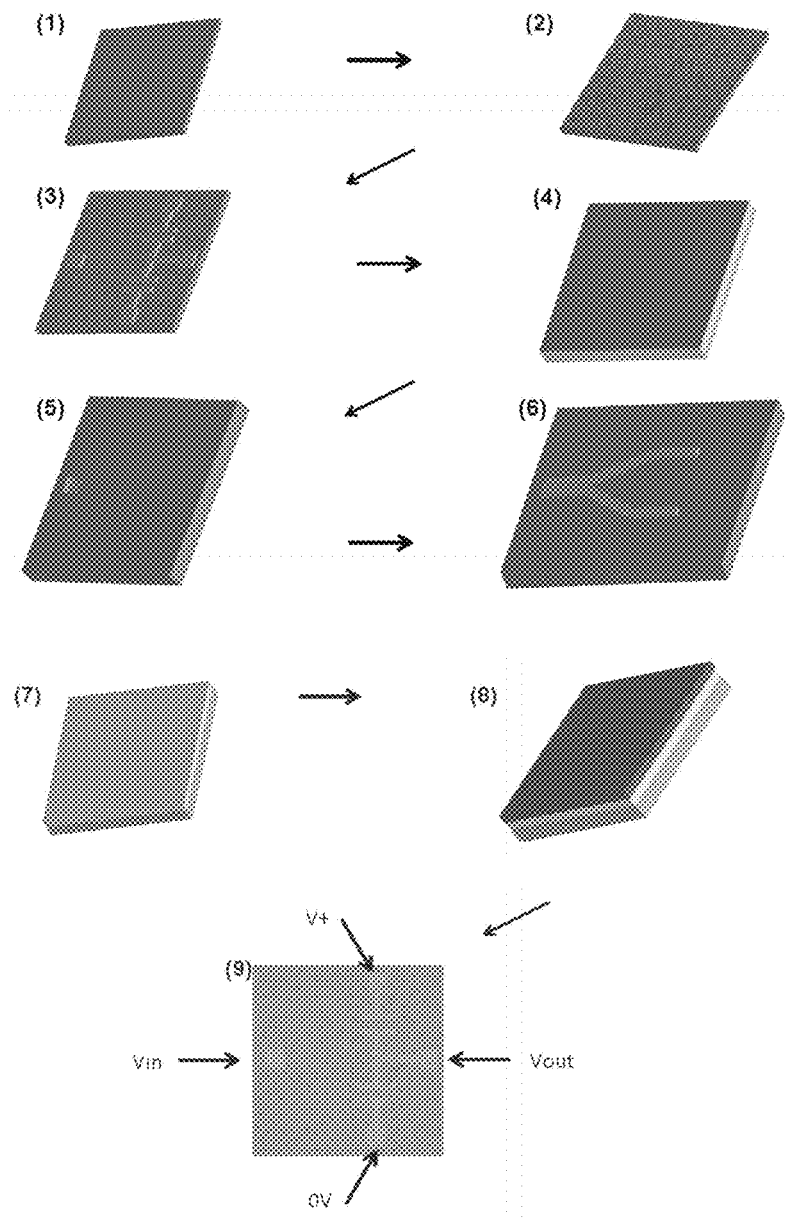
Figure 8:
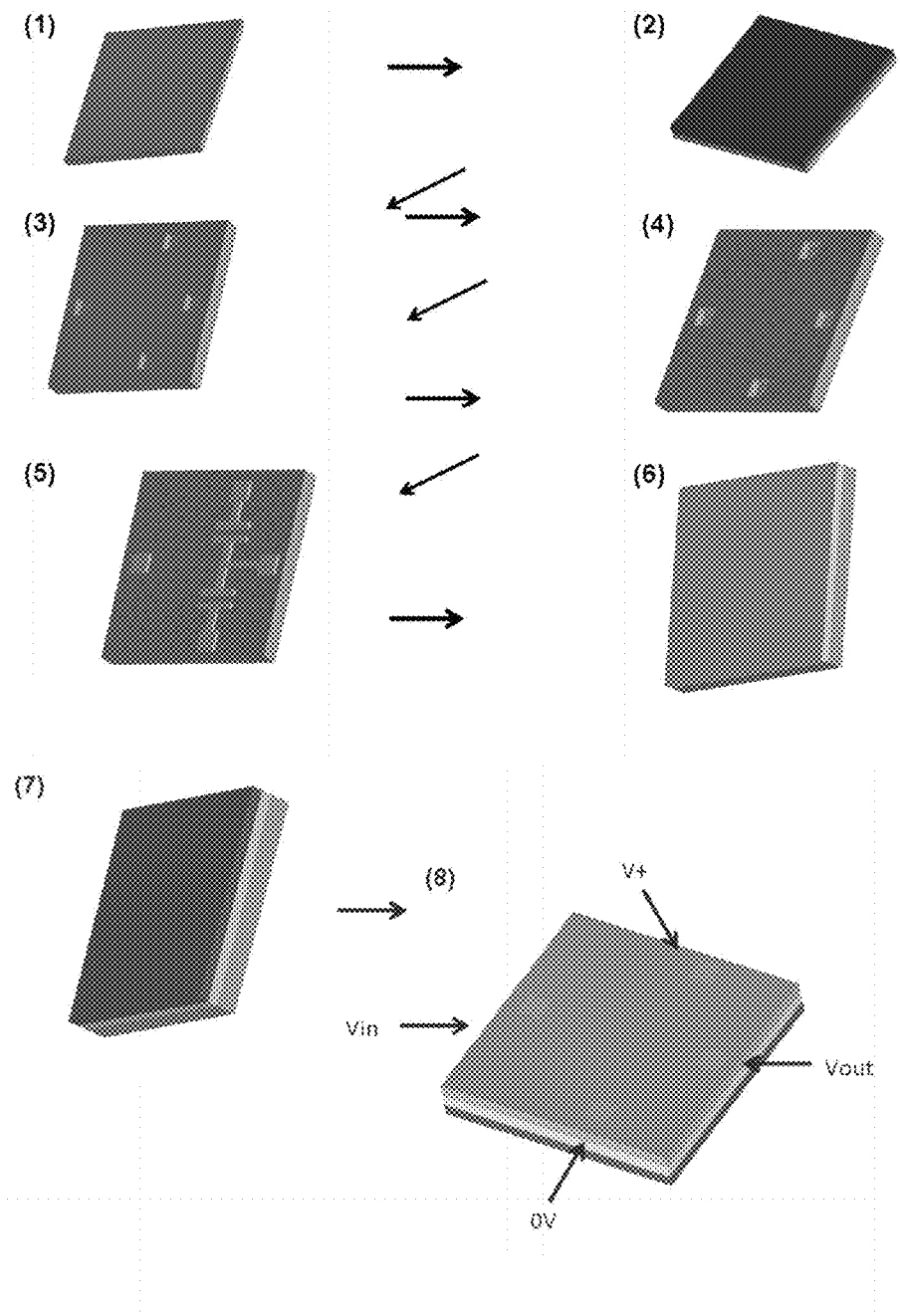
Figure 9:
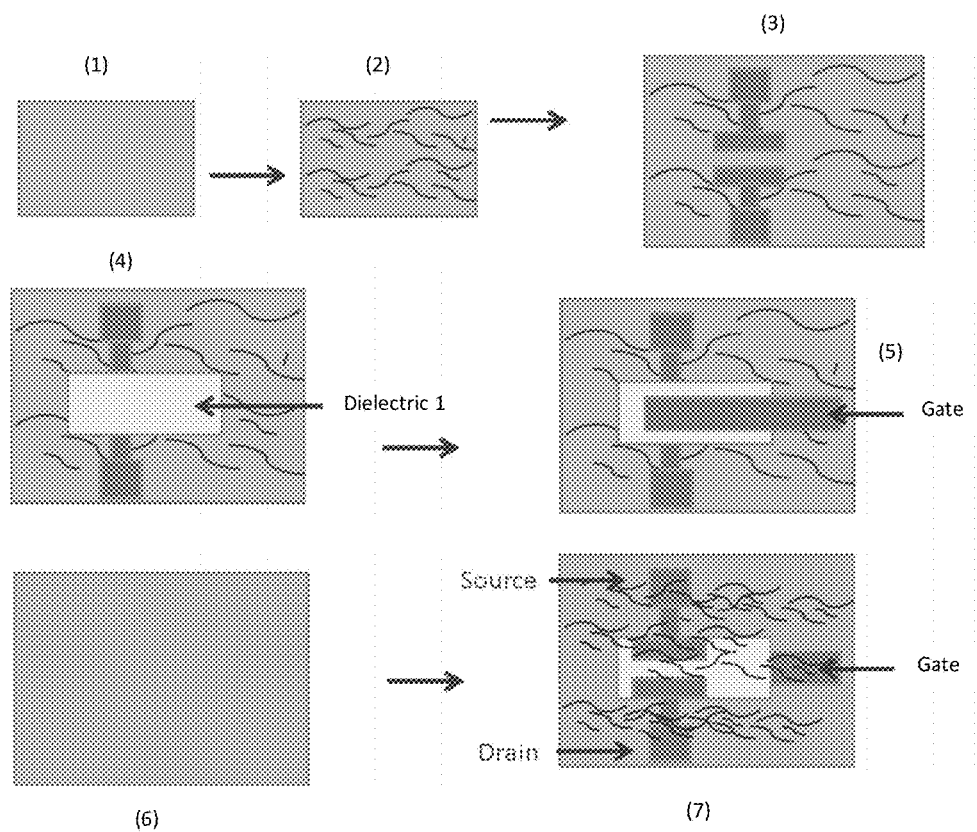
Figure 10:
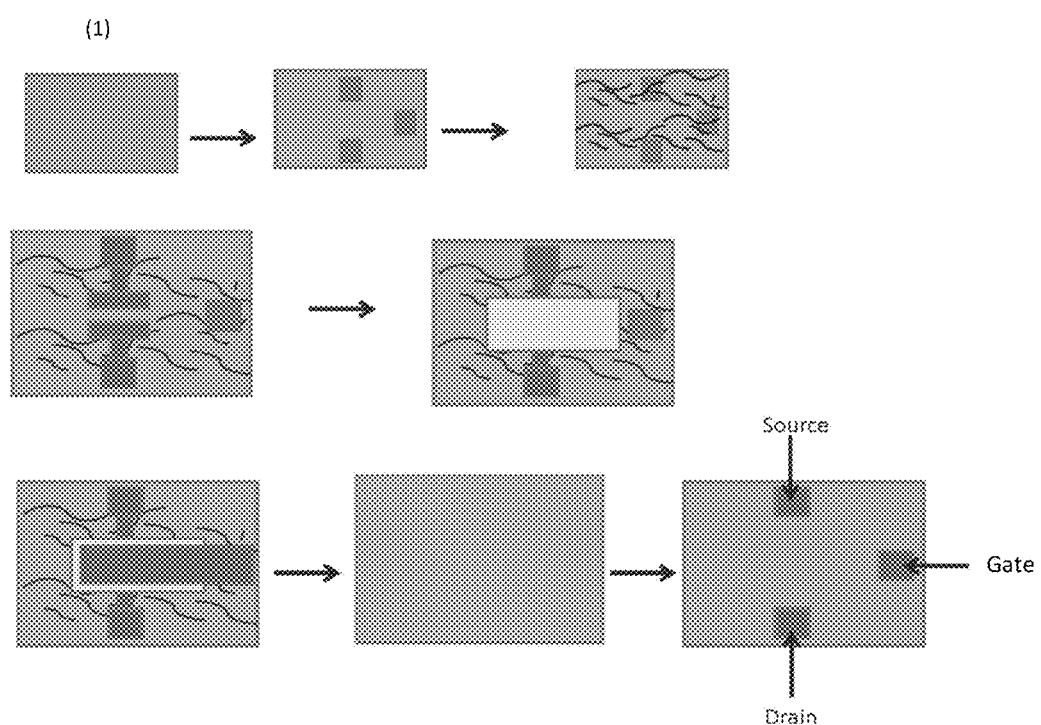
Figure 11:
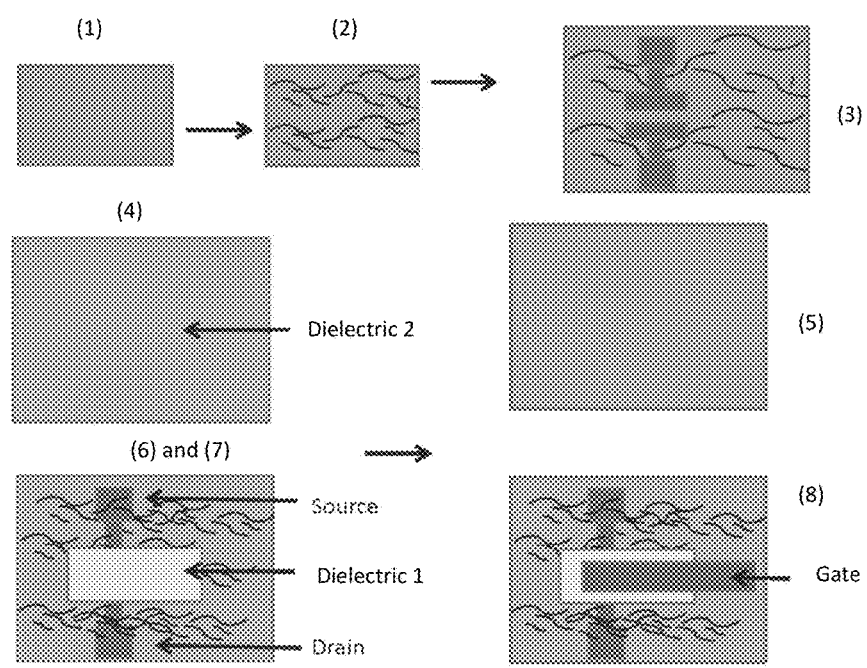
Figure 12:
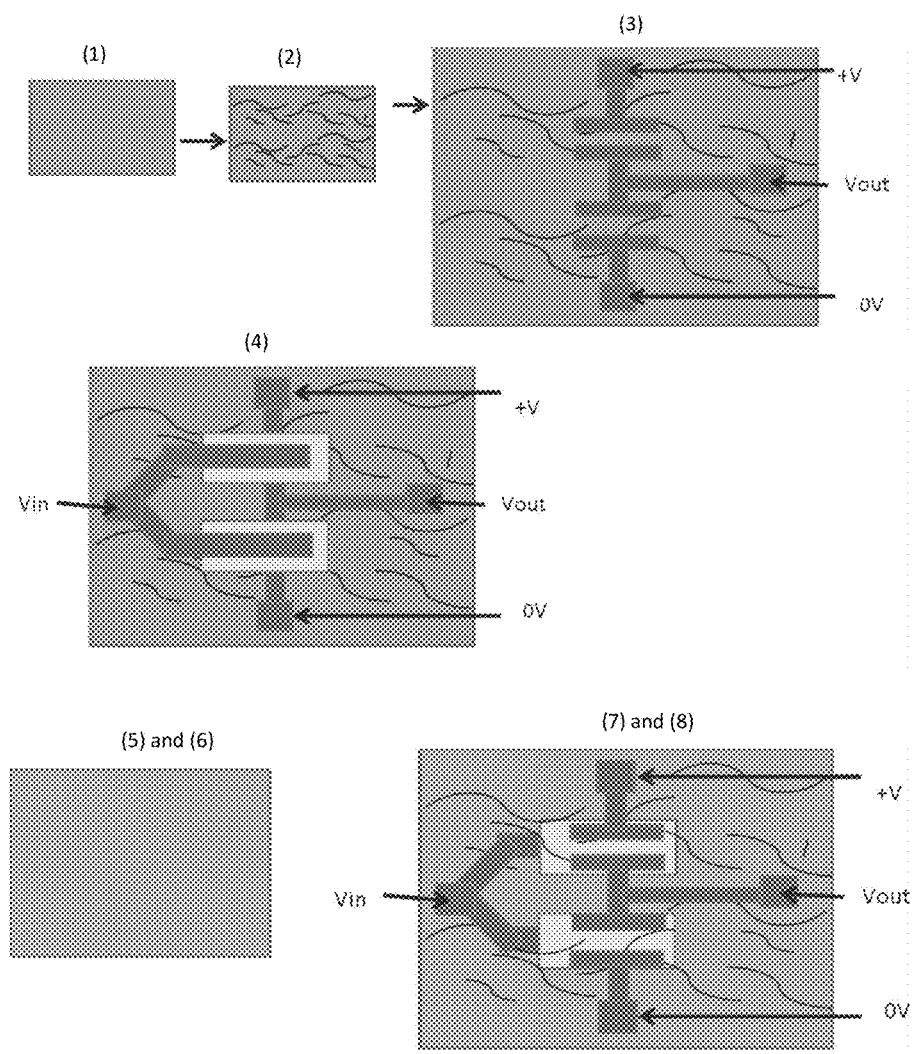

A better understanding of the invention will be obtained and other characteristics and advantages of the invention will become more clearly apparent on reading the explanatory description which follows and which refers to the figures, in which:

FIG. 1 diagrammatically represents a transistor, comprising a flexible substrate, obtained by a process of the prior art, FIG. 2 diagrammatically represents a transistor obtained by the process of the invention, before step f) of the process of the invention, FIG. 3 represents a transistor, obtained by the process of the invention, FIG. 4 diagrammatically represents the different steps of synthesis of the carbon nanotubes, according to a particularly advantageous embodiment of the process of the invention, FIG. 5 diagrammatically represents the different steps of manufacture of a bottom-gate transistor by lithography according to the process of the invention, FIG. 6 represents the different steps of manufacture of a top-gate transistor by lithography according to an embodiment of the process of the invention, FIG. 7 diagrammatically represents the different steps of manufacture of an inverter without a layer made of a dielectric material between the support and the active layer, according to an embodiment of the process of the invention, FIG. 8 diagrammatically represents the different steps of manufacture of an inverter with a layer made of a dielectric material between the support and the active layer, according to an embodiment of the process of the invention, FIG. 9 diagrammatically represents the different steps of manufacture of a bottom-gate transistor by inkjet printing according to an embodiment of the process of the invention, FIG. 10 diagrammatically represents the different steps of manufacture of a bottom-gate transistor by inkjet printing according to another embodiment of the process of the invention, FIG. 11 diagrammatically represents the different steps of manufacture of a top-gate transistor by inkjet printing according to an embodiment of the process of the invention, and FIG. 12 diagrammatically represents the different steps of manufacture of an inverter by inkjet printing according to an embodiment of the process of the invention.

The process for the manufacture of a transistor on a flexible substrate according to the prior art will be described in reference to the appended FIG. 1.

The different steps of this manufacturing process are as follows.

A flexible substrate made of PET, denoted 100 in FIG. 1, is adhesively bonded to one face of a rigid support, denoted 500 in FIG. 1, for example made of metal, provided on a gate, denoted 401 in FIG. 1 and formed on the opposite face of the substrate 100.

Subsequently, an active layer, denoted 300 in FIG. 1, made of a semiconductor material, is formed on the surface of the flexible substrate 100 on which the gate 401 is positioned. It can be a layer made of carbon nanotubes forming a percolating network. These carbon nanotubes were grown beforehand on a different substrate and transferred onto the surface of the substrate 100.

The source and drain electrodes, respectively denoted 402 and 403 in FIG. 1, are then formed on the free surface of the active layer 300.

Finally, a layer, denoted 600 in FIG. 1, made of an insulating protective material, is deposited over the entire free surface of the layer 300 and over the source and drain electrodes 402 and 403. This layer 600 can, for example, be made of polymethyl methacrylate (PMMA).

Thus, in the processes of the prior art, when a flexible substrate, such as a substrate made of a material comprising an organic part, such as a polymer, and the like, or made of paper, or also made of an inexpensive substrate, such as glass or paper (which is both flexible and inexpensive), is used, the deposition of the different components of the electronic device takes place on the desired final substrate of the electronic device. Furthermore, in the processes of the prior art, when the conditions for the manufacture of one or more of the components of the final electronic device, such as the temperature, the use of acid, and the like, would damage or destroy the final substrate, it is necessary to manufacture this component, or these components, requiring the use of such conditions, on a separate substrate and to transfer this (or these) component(s) onto the desired final substrate.

In contrast, in the process of the invention, the layer forming the substrate is only deposited in the end, after the formation of all the different components of the electronic device (active layer, source electrode, drain electrode, top or bottom gate, and the like); the formation of this active layer and of all the different components of the electronic device takes place on one and the same support, which will subsequently be removed.

Thus, in the process of the invention, none of the components of the electronic device is manufactured on a separate substrate and subsequently transferred onto the substrate which will be removed.

In other words, all the components of the electronic device manufactured by the process of the invention are formed in the substrate which will subsequently be removed or on one of the layers deposited on this substrate.

More specifically, and as shown in FIGS. 2 and 3, the first step of the process of the invention consists of the provision of a support, denoted 10 in FIGS. 2 and 3, this support subsequently being intended to be removed.

This support is preferably made of a salt of an alkali metal or alkaline earth metal. This is because this makes it possible to easily remove it by simple dissolution.

Furthermore, with such materials, the desired stiffness and the desired flatness can easily be obtained. Furthermore, they are inexpensive materials.

The salts of alkali metals or alkaline earth metals which can be used are all the salts, such as chloride, bromide, fluoride, iodide, carbonate, oxide or hydroxide salts of alkali metals or alkaline earth metals, such as magnesium, sodium or potassium.

Preferably, the support 10 is made of sodium chloride (NaCl) or of potassium chloride (KCl).

Most preferably, the support 10 is made of sodium chloride.

The second step of the process of the invention is an optional step of deposition, on one face of the support 10, of a layer, denoted 2 in FIGS. 2 and 3, made of a dielectric material. This layer serves to insulate the support 10 from layers which will subsequently be deposited or formed on this support 10.

The dielectric materials which can be used to form this layer 2 are all dielectric materials known to a person skilled in the art.

More preferably, the dielectric material concerned will be alumina ($Al_2O_3$) or silica ($SiO_2$).

Most preferably, the layer of dielectric material 2 will be made of silica.

The second step (if the step of deposition of the layer 2 is not carried out) or the third step (if the step of deposition of the layer made of dielectric material is carried out) of the process of the invention is a step of deposition of an active layer, denoted 3 in FIGS. 2 and 3, made of a semiconductor material.

This layer can be made of any desired semiconductor material, such as silicon, silicon carbide, alloys of silicon and germanium, germanium, the different forms of carbon, such as graphene and single- or multi-walled carbon nanotubes, tetracene, anthracene, fullerenes or also organic semiconductor polymers, such as polythiophene, poly(3-hexylthiophene) (P3HT), poly[N-9'-heptadecanyl-2,7-carbazole-alt-5,5-(4',7'-di-2-thienyl-2',1',3'-benzothiadiazole)] (PCDTBT), poly[2-methoxy-5-(3',7'-dimethyloctyloxy)-1,4-phenylene-vinylene] (MDMO-PPV), poly[2-methoxy-5-(2-ethylhexyloxy)-1,4-phenylene-vinylene] (MEH-PPV), poly(3,4-ethyl-enedioxythiophene) (PEDOT), poly(3,4-ethylenedioxythiophene):poly(styrenesulfonate) (PEDOT:PSS), fullerenes, methyl [6,6]-phenyl-$C_{61}$-butyrate (PCBM), poly[oxa-1,4-phenylene-(1-cyano-1,2-vinylene)-(2-methoxy-5-(3,7-dimethyloctyloxy)-1,4-phenylene)-1,2-(2-cyanovinylene)-1,4-phenylene] (PCNEPV), polyfluorene and poly(styrenesulfonate) (PSS).

In the invention, it is particularly advantageous to form a layer made of single-walled carbon nanotubes.

This is because it is possible, in a particularly preferred embodiment of the process of the invention, to directly grow the carbon nanotubes on the substrate 10 or on the layer 2, according to whether the step of deposition of the layer 2 is or is not carried out, which makes it possible to obtain aligned carbon nanotubes which have not been cut during their transfer, as takes place in the case of the prior art.

This greatly improves the overall properties thus obtained of the electronic device.

However, the carbon nanotubes can also be transferred, after having been grown on a separate substrate, in order to form a percolating network.

When the carbon nanotubes are grown directly on the support 10 or the layer 2, the growth process is carried out as represented diagrammatically in FIG. 4.

During the first step, the surfaces of the support (10) (salt) or of the layer 2 (salt) with an insulating layer) are functionalized by coordinating organic groups (pyridines) obtained by silanization (FIG. 4, step 1). The silanes used are presented below:

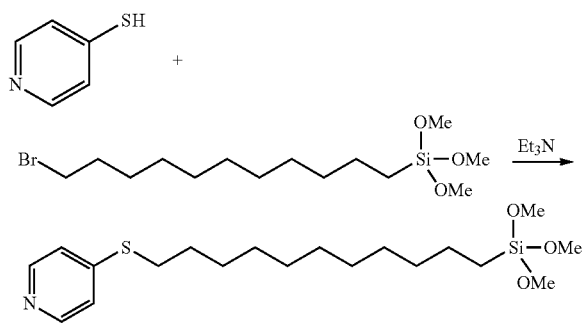

These surfaces will subsequently be used for the deposition by self-assembling of a monomolecular layer of one (or more) metal complex(es) (e.g.: Fe, Ru, Co, and the like) (FIG. 4, step 2). The controlled pyrolysis (under hydrogen) of this self-assembled layer of metal complexes subsequently makes it possible to convert them into metal nanoparticles of catalysts (FIG. 4, step 3). The control of the density of metal on the surface and also their diameter is given, on the one hand, by the geometric surface area of the ligand used (which will make possible the exchange between the pyridine end group of the silane molecule and the metal complex deposited by self-assembly) and, on the other hand, by the number of grafting sites present on the surface. This will consequently make it possible to obtain a dilute blanket of NTCs on the surface.

The nonfunctionalized surfaces do not exhibit any metal deposit. The advantage of this approach is the control of the density and the position of catalyst on the surface, characteristics which must be considered when the incorporation of the nanomaterials in devices is envisaged. After this step, the carbon nanotubes will be synthesized by hot filament chemical vapor deposition (HFCVD under hydrogen and methane) (FIG. 4, step 4).

Of course, in order to form the desired device, it is necessary to form beforehand different components of the electronic device, on the support 10 or the layer 2, before the step of formation of the layer 3, this is carried out.

This is because the following step of the process of the invention is the formation of the different components of the device on and/or under the layer 3.

Finally, a protective layer, denoted 1 in FIGS. 2 and 3, is deposited on the stack of layers obtained, this protective layer being made of the material M desired to form the substrate 1 of the electronic device.

Thus, this layer 1 can be made of a flexible material, such as a paper sheet, a polymer, such as polyimide, polyethylene terephthalate (PET), polyethylene naphthalate (PEN), polyvinyl chloride or poly(methyl methacrylate) (PMMA), or also an inexpensive material, such as, again, a paper sheet or glass or metal.

The final step of the process of the invention is then to remove the support 10, and the electronic device shown in FIG. 3 is obtained by turning the structure obtained upside down. This device comprises the flexible substrate 1 and the active layer 3, in particular made of single-walled carbon nanotubes.

It will be easily understood that, although the process of the invention is particularly advantageous when it is desired to form an electronic device having a flexible substrate or made of an inexpensive material not withstanding high synthesis temperatures, it can also be used with other substrates of any type, such as a silicon wafer, and the like.

This is because the essential point of the process of the invention is the formation of the different layers and components of the electronic device on a support which is subsequently removed and the formation of the substrate in the last step, which makes it possible not only to grow the carbon nanotubes directly in situ, without proceeding to the transfer from a different substrate, but also to use all the desired methods for the formation of the different components of the electronic device.

Thus, in order to form the different components of the electronic device, which are denoted 4 in FIGS. 2 and 3, it will be possible to use all the desired methods, such as inkjet printing, lithographic printing, etching printing, and the like, without having to worry about the temperature of deformation of the substrate.

In order to achieve a better understanding of the invention, a description will now be given, as purely illustrative and nonlimiting examples, of several implementational examples thereof.

EXAMPLE 1: MANUFACTURE OF A BOTTOM-GATE TRANSISTOR

1) Provision of a support 10 made of NaCl. It can also be made of KCl (step a) of the process of the invention). This support is inexpensive and ecological.

2) The single-walled carbon nanotubes (SWNTs) (the active semiconductor layer 3) are synthesized by the method described above (step c) of the process of the invention).

3) The electrodes (respectively bearing the names of drain (D), of source (S) and of gate (G)) (the components 4) are formed by standard lithography (resin treatment, then the insulation of the sample to a first lithography mask, evaporation of metal, liftoff). They can also be formed by much simpler and less expensive methods, carried out at ambient temperature and atmospheric pressure, such as UV (Ultraviolet) lithography. The gap between the drain electrode and the source electrode is of the order of 1 to 20 μm and the width of the electrodes is of the order of a few microns to a few millimeters. At this step, the spacing between the (drain and source) electrodes is preferably chosen in order to prevent the probability of having percolations between the carbon nanotubes, that is to say to have exclusively carbon nanotubes which directly interconnect the electrodes. The thickness of D, S and G is the same (a few nm to a few tens of nm), in order to thus have a uniform dielectric deposit subsequently.

4) The deposition of a layer 2 made of a dielectric material ($SiO_2$), which serves to insulate the carbon nanotubes from the gate, is carried out. The thickness of the layer 2 in this step is preferably from a few nanometers to a few hundred nanometers, in order to have high performance transistors, as the use of greater thicknesses requires the application of a high voltage to harvest only a low current.

5) In order to open a window which will give access to the gate contact, reactive ion dry etching of the surface by plasma (e.g.: by oxygen) or wet etching is carried out. This operation is carried out using a second mask.

6) The deposition of the gate is carried out using a third mask.

7) A second insulator is deposited by evaporation. In order to render the surface uniform, mechanical polishing can be carried out. This layer serves as a layer for attaching/adhesive bonding of final transfer substrate 1, for example the glass (step e) of the process of the invention).

The above steps 3) to 6) correspond to step d) of the process of the invention.

8) Dissolution of the synthesis support 10 (step f) of the process of the invention).

9) After the dissolution, the step of connecting the electrodes is carried out by a fourth mask.

It is clearly apparent that a transfer substrate 1 can also be deposited uniformly over the entire surface of the electronic devices obtained by the process of the invention by:
  spin coating, in the case of a substrate made of a material comprising an organic part, such as PMMA,
  evaporation, in the case of a metal.

EXAMPLE 2: MANUFACTURE OF A BOTTOM-GATE TRANSISTOR BY LITHOGRAPHY

The different manufacturing steps are presented diagrammatically in FIG. 5.

1) Provision of a support 10 made of KCl (step a) of the process of the invention).

2) Deposition of a layer 2 made of $Al_2O_3$ by evaporation on the support 10 (step b) of the process of the invention).

3) Opening of windows, by plasma etching, which determine the respective location and the respective size of the (drain, source and gate) electrodes, using a first mask (step d) of the process the invention).

4) Synthesis of single-walled carbon nanotubes (SWNTs) (step e) of the process of the invention).

5) Deposition of the (drain, source and gate) electrodes of the same thickness with a second mask.

6) Evaporation of a second dielectric material, such as $Al_2O_3$ or $SiO_2$.

7) Opening of a window, by a second plasma etching (e.g.: by oxygen), which will give access to the gate contact. This operation was carried out using a third mask.

8) Deposition of the gate using a fourth mask.

The above steps 5) to 8) form, in combination with the above step 3), step d) of the process of the invention.

9) Deposition of a third insulating material, which serves as an attaching layer, by evaporation, followed by a mechanical polishing in order to render the surface uniform.

10) Deposition of the transfer substrate uniformly over the entire surface, either by:
  spin coating, in the case of plastic (e.g. PMMA),
  adhesive bonding, in the case of glass,
  evaporation, in the case of metal (step e) of the process of the invention).

11) Dissolution of the synthesis support 10 (step f) of the process of the invention).

12) Connection of the electrodes by a fifth mask.

EXAMPLE 3: MANUFACTURE OF A TOP-GATE TRANSISTOR BY LITHOGRAPHY

The different manufacturing steps are shown diagrammatically in FIG. 6.

1) Provision of a support 10 made of KCl or NaCl as synthesis substrate.
2) Evaporation of a first dielectric material (layer 2). This layer 2 will subsequently serve as an insulator of NTCs and of the gate.
3) Delimitation of the location and of the size of the (drain and source) electrodes by dry or wet plasma etching. In this step, the distance between the drain and source electrodes is chosen in such a way that the NTCs interconnect directly with the electrodes. This step is carried out by conventional lithography with a first masking level.
4) Synthesis of carbon nanotubes (layer 3).
5) Deposition of the (drain and source) electrodes (using a second masking step) by evaporation.
6) Evaporation of a second dielectric material; the latter serves as a transfer substrate attaching layer. After this step, a mechanical polishing will be carried out in order to thus render the surface uniform.
7) Deposition of the transfer substrate 1 (plastic, glass, metal, and the like).
8) Dissolution of the synthesis support 10.
9) Evaporation of the gate by a third mask. After this step, a step of connection of the electrodes by a fourth mask is necessary.

EXAMPLE 4: MANUFACTURING OF A TOP-GATE TRANSISTOR

The procedure as in example 3 is carried out, except that the source and drain electrodes are functionalized with poly(ethyleneimine) (PEI) before step 6. This functionalization makes it possible to change from a transistor having behavior of "p" type to a transistor having behavior of "n" type or in order to produce an ambipolar transistor.

EXAMPLE 5: MANUFACTURE OF A TOP-GATE TRANSISTOR

The procedure as in example 3 is carried out, except that, before step 6), the metal of the electrode is chosen in order to obtain a work function close to that obtained with carbon nanotubes.

In theory, any metal can be used but the preferred metal is palladium as it exhibits elevated properties of injection of the charges, a high corrosion resistance, and the like.

EXAMPLE 6: MANUFACTURE OF A TOP-GATE TRANSISTOR

The procedure as in example 3 is carried out, except that, before step 6), a step of localized deposition of a compound, such as potassium, is carried out.

In this example, instead of carrying out an evaporation of the metal (in this instance potassium) over a large surface with an evaporator, a localized deposition of this metal, by inkjet printing, is carried out.

EXAMPLE 7: MANUFACTURE OF A SENSOR

The procedure as in example 1 is carried out, except that an additional step of functionalization of the surface of the electrodes by the desired chemical substances (those intended to detect and/or quantify the desired compound) is carried out after step 9) of dissolution of the support 10.

EXAMPLE 8: MANUFACTURE OF AN INVERTER WITHOUT LAYER 2 MADE OF A DIELECTRIC MATERIAL

The different steps of this manufacturing operation are represented diagrammatically in FIG. 7.

1) Provision of a support 10 made of NaCl as synthesis substrate.
2) Synthesis of carbon nanotubes (layer 3).
3) Evaporation of the (drain and source) electrodes of the two transistors, of $V_{in}$ contact and of contact of the gate using a first mask (layer 4).
4) Evaporation of a first dielectric material.
5) Opening of a window by a plasma etching (e.g.: by oxygen), which will give access to the gate contact. This operation is carried out using a second mask.
6) Deposition of the gate and of the $V_{in}$ contact using a third mask.
7) Evaporation of a second dielectric material. The latter serves as an attaching layer on the transfer substrate 1. After this step, a mechanical polishing is carried out in order to thus render the surface uniform.
8) Deposition of the transfer substrate 1 (plastic, glass, metal, and the like).
9) Dissolution of the synthesis support 10.
10) Functionalization of one of the two transistors.
11) Connection of the electrodes.

EXAMPLE 9: MANUFACTURE OF AN INVERTER WITH LAYER 2 MADE OF A DIELECTRIC MATERIAL

The different steps of this manufacturing operation are represented diagrammatically in FIG. 8.

1) Provision of a support 10 made of KCl or NaCl as synthesis substrate.
2) Deposition of dielectric ($Al_2O_3$ or $SiO_2$, and the like) by evaporation on the support 10.
3) Opening of windows (S, D, Vin and Vout) by plasma etching (e.g.: by oxygen). This operation is carried out using a first mask.
4) Synthesis of the carbon nanotubes (layer 3).
5) Evaporation of the (drain and source) electrodes of the two transistors, of $V_{in}$ contact and of contact of the gate using a second mask or functionalization of one of the two transistors (layer 4).
6) Evaporation of a second dielectric material. After this step, a mechanical polishing is carried out in order to render the surface uniform.
7) Deposition of the transfer substrate 1 (plastic, glass, metal, and the like).
8) Dissolution of synthesis support 10, followed by a step of connection of the electrodes.

EXAMPLE 10: MANUFACTURE OF A BOTTOM-GATE TRANSISTOR BY INKJET PRINTING

The different steps of this manufacturing operation are represented diagrammatically in FIG. 9.

1) Provision of a support 10 made of KCl or NaCl.
2) Synthesis of single-walled carbon nanotubes (SWNTs) (layer 3).

3) Localized deposition of the (drain and source) electrodes.

4) Localized deposition of the first dielectric (e.g.: $Al_2O_3$ or $SiO_2$).

5) Localized deposition of the gate.

The above steps 3), 4) and 5) correspond to step d) of the process of the invention.

6) Deposition of a second dielectric or plastic material, for example poly(methyl methacrylate) (PMMA), for example by spin coating. This layer subsequently serves as an attaching layer for the transfer substrate 1, followed by a mechanical polishing in order to render the surface uniform.

7) The deposition of the transfer substrate 1 uniformly over the entire surface is carried out either by:
 spin coating, in the case of plastic (e.g.: PMMA),
 adhesive bonding, in the case of glass or other substrate,
 evaporation, in the case of metal.

8) Dissolution of the synthesis support 10, followed by a step of connection of the electrodes.

EXAMPLE 11: MANUFACTURE OF A BOTTOM-GATE TRANSISTOR

The procedure as in example 10 is carried out.

Thus, the following steps are carried out:

1) Provision of a support 10 made of KCl or NaCl.

2) Deposition of a dielectric material with three regions, respectively corresponding to the regions desired for the deposition of the drain and source electrodes and of the gate, without dielectric material.

3) Synthesis of the single-walled carbon nanotubes (SWNTs).

4) Deposition of the drain and source electrodes in the regions not covered with dielectric material in step 2).

5) Localized deposition of a dielectric material, such as $Al_2O_3$ or $SiO_2$, between the two electrodes deposited in step 4).

6) Deposition of the gate in the third region not covered with dielectric material in step 2).

7) Localized deposition of a dielectric material other than a dielectric material deposited in step 5), followed by a mechanical polishing in order to render the surface uniform.

8) Deposition of the transfer substrate uniformly over the entire surface by:
 spin coating, in the case of a plastic, such as PMMA,
 adhesive bonding, in the case of glass, paper or other,
 evaporation, in the case of a metal.

9) Dissolution of the support 10 made of KCl or NaCl, and

10) Connection of electrodes.

EXAMPLE 12: MANUFACTURE OF A BOTTOM-GATE TRANSISTOR

The different steps of this manufacturing operation are represented diagrammatically in FIG. 10.

1) Provision of a support 10 made of KCl or NaCl

2) Localized deposition of three regions (corresponding to the locations of the D, S and G electrodes) made of a dielectric material (layer 2).

3) Synthesis of single-walled carbon nanotubes (SWNTs) (layer 3).

4) Localized deposition of the (drain and source) electrodes.

5) Localized deposition of the first dielectric material (e.g.: $Al_2O_3$ or $SiO_2$) between the two electrodes.

Steps 4) and 5) correspond to step d) of the process of the invention.

6) Deposition of a second dielectric material, followed by a mechanical polishing in order to render the surface uniform.

7) The deposition of the transfer substrate 1 uniformly over the entire surface is carried out either by:
 spin coating, in the case of plastic (e.g.: PMMA),
 adhesive bonding, in the case of glass or other substrate,
 evaporation, in the case of metal.

8) Dissolution of synthesis support 10, followed by a step of connection of the electrodes.

EXAMPLE 13: MANUFACTURE OF A TOP-GATE TRANSISTOR

The different steps of this manufacturing operation are represented diagrammatically in FIG. 11.

1) Provision of a support 10 made of KCl or NaCl as synthesis substrate.

2) Synthesis of carbon nanotubes (layer 3).

3) Localized deposition of the (drain and source) electrodes (step d) of the process of the invention).

4) Deposition of a second dielectric material; the latter serves as an attaching layer on the transfer substrate 1. After this step, a mechanical polishing is carried out in order to render the surface uniform.

5) Deposition of the transfer substrate 1 (plastic, glass, metal, and the like).

6) Dissolution of the synthesis support 10.

7) Deposition of a localized layer of the first dielectric material; the latter will subsequently serve as an insulator of the NTCs and of the gate.

8) Localized deposition of the gate.

9) Connection of the electrodes.

EXAMPLE 14: MANUFACTURE OF A BOTTOM-GATE TRANSISTOR

The procedure as in example 10 is carried out, except that an additional step of functionalization of the NTCs is carried out after step 8) of dissolution of the synthesis support 10.

EXAMPLE 15: MANUFACTURE OF A TOP-GATE TRANSISTOR

The procedure as in example 13 is carried out, except that an additional step of functionalization of the NTCs is carried out after step 2) of synthesis of single-walled carbon nanotubes (SWNTs).

This functionalization is carried out in order to render the transistor sensitive to a precise molecule, a precise element or a precise compound (to render the sensor selective). Thus, the functionalization will be carried out with a chemical molecule which makes it possible to detect the desired compound(s).

EXAMPLE 16: MANUFACTURE OF A SENSOR

The procedure as in example 10 is carried out, except that an additional step of functionalization of the NTCs is carried out in step 8).

This functionalization is carried out for the same purpose as the transistor of example 15.

EXAMPLE 17: MANUFACTURE OF AN INVERTER

The different steps of this manufacturing operation are represented diagrammatically in FIG. 12.

1) Provision of a support 10 made of KCl or NaCl as synthesis substrate.

2) Synthesis of carbon nanotubes (layer 3).

3) Localized deposition of the (drain and source) electrodes of the two transistors and the $V_{out}$ contact.

4) Localized deposition of the first dielectric material, gate electrode and $V_{in}$ contact.

Steps 2) and 3) correspond to step d) of the process of the invention.

5) Localized deposition of the second dielectric material; the latter serves as an attaching layer on the transfer substrate 1. After this step, a mechanical polishing is carried out in order to render the surface uniform.

6) Deposition of the transfer substrate 1 (plastic, glass, metal, and the like).

7) Dissolution of the synthesis support 10.

8) Functionalization of one of the two transistors, followed by a step of connection of the electrodes.

The invention claimed is:

1. A process of manufacturing an electronic device comprising:
   a substrate comprising a material M selected from the group consisting of a flexible material, a metal, a glass and a paper, and
   an active layer comprising a semiconductor material,
   wherein the process comprises:
   (a) providing a support comprising a salt of an alkali metal or alkaline earth metal as a synthesis substrate,
   (b) optionally depositing a layer comprising a dielectric material on one face of the support,
   (c) forming the active layer comprising the semiconductor material, either on one face of the support when step (b) is not carried out, or on the face of the layer deposited in step (b) opposite to the face of the layer in contact with the support, when step (b) is carried out,
   (d) forming the desired components of the electronic device on and/or under the active layer formed in step (c), thereby obtaining a stack of layers and desired components of the electronic device, on the support comprising the salt of alkali metal or alkaline earth metal,
   (e) depositing a protective layer on the stack obtained in step
   (d) of layers and of the different components of the electronic device, said protective layer comprising the material M suitable for the substrate, and
   (f) removing the support, and
   turning the structure obtained in step (f) upside down thereby obtaining the desired electronic device, and
   wherein the process does not comprise any step of manufacturing one or more of the different components of said electronic device on a substrate other than the support nor any step of transfer of the structure obtained in step (f) on a substrate different from the support.

2. The process as claimed in claim 1, characterized in that the support comprises a salt selected from the group consisting of chloride, bromide, fluoride, iodide, oxide, hydroxide and carbonate salts of an alkali metal or alkaline earth metal selected from the group consisting of magnesium, sodium and potassium.

3. The process as claimed in claim 1, characterized in that the layer is comprises a dielectric material selected from the group consisting of $Al_2O_3$ and $SiO_2$.

4. The process as claimed in claim 1, characterized in that the active layer comprises a material selected from the group consisting of graphene, carbon nanotubes, silicon, germanium, alloys of silicon and germanium, silicon carbide and organic semiconductor materials.

5. The process as claimed in claim 1, characterized in that the active comprises single-walled carbon nanotubes.

6. The process as claimed in claim 5, characterized in that the active layer of carbon nanotubes is obtained by growth of the carbon nanotubes directly on the surface of the support when step (b) is not carried out or directly on the face of the layer deposited in step (b) opposite to the face of the layer in contact with the support when step (b) is carried out.

7. The process as claimed in claim 1, characterized in that the electronic device is a transistor.

8. The process as claimed in claim 1, characterized in that the electronic device is a sensor comprising electrodes and in that it additionally comprises, after step (f), a step of functionalization of the electrodes with the desired substances.

9. The process as claimed in claim 1, characterized in that the electronic device is an inverter.

10. The process as claimed in claim 1, wherein the flexible material comprises an organic part.

11. The process as claimed in claim 10, wherein the organic part is selected from the group consisting of polyimide, polyethylene terephthalate (PET), polyethylene naphthalate (PEN), polyvinyl chloride and poly(methyl methacrylate) (PMMA).

12. The process as claimed in claim 2, wherein the support comprises NaCl or KCl.

13. The process as claimed in claim 4, wherein the carbon nanotubes are single-walled carbon nanotubes.

14. The process as claimed in claim 4, wherein the organic semiconductor materials are selected from the group consisting of tetracene, anthracene, polythiophene, poly(3-hexylthiophene) (P3HT), poly[N-9'-heptadecanyl-2,7-carbazole-alt-5,5-(4',7' di-2-thienyl-2',1',3'-benzothia¬diazole)] (PCDTBT), poly[2-methoxy-5-(3',7'-dimethyloctyloxy)-1,4-phenylene-vinylene] (MDMO-PPV), poly[2-methoxy-5-(2-ethylhexyloxy)-1,4-phenylene-vinylene] (MEH-PPV), poly(3,4-ethylenedioxythiophene) (PEDOT), poly(3,4-ethyl¬enedioxythiophene):poly(styrenesulfon-ate) (PEDOT:PSS), fullerenes, methyl [6,6]-phenyl-C61-butyrate (PCBM), poly[oxa-1,4-phenylene-(1-cyano-1,2-vinylene)-(2-methoxy-5-(3,7-dimethyloctyloxy)-1,4-phenylene)-1,2-(2-cyanovinylene)-1,4-phenylene] (PCNEPV), polyfluorene and poly(styrenesulfonate) (PSS).

* * * * *